US005773695A

United States Patent [19]

Thompson et al.

[11] Patent Number: 5,773,695
[45] Date of Patent: Jun. 30, 1998

[54] PLANT NUCLEAR SCAFFOLD ATTACHMENT REGION AND METHOD FOR INCREASING GENE EXPRESSION IN TRANSGENIC CELLS

[75] Inventors: William F. Thompson, Raleigh, N.C.; Gerald Hall, Jr., Madison, Wis.; Steven Spiker; George C. Allen, both of Raleigh, N.C.

[73] Assignee: North Carolina State University, Raleigh, N.C.

[21] Appl. No.: 592,658

[22] Filed: Jan. 26, 1996

[51] Int. Cl.⁶ ........................................... A01H 1/04
[52] U.S. Cl. .................. 800/205; 435/172.3; 435/320.1; 435/414; 435/419; 536/23.1; 536/24.1
[58] Field of Search ................................. 536/23.1, 24.1; 435/320.1, 240.4, 414, 419, 172.3; 800/205

[56] References Cited

U.S. PATENT DOCUMENTS 5,459,252  10/1995  Conkling et al. .................. 536/24.1

FOREIGN PATENT DOCUMENTS

WO 94/07902  4/1994  WIPO.

OTHER PUBLICATIONS

G.C. Allen et al., Scaffold Attachment Regions Increase Reporter Gene Expression in Stably Transformed Plant Cells, *Plant Cell* 5:603–613 (1993).
G.C. Allen et al., Abstract, *4th International Congress of Plant Molecular Biology*, Amsterdam (1994).
G.E. Hall et al., Abstract, *Annual Meeting of the Society of Plant Physiologists*, Portland, OR (1994).
M.A. Conkling et al., Isolation of Transcriptionally Regulated Root–specific Genes from Tobacco, *Plant Physiol.* 93:1203–1211 (1990).
G.E. Hall et al., Nuclear Scaffold and Scaffold–Attachment Regions in Higher Plants, *Proc. Natl. Acad. Sci.* 88:9320–9324 (1991).
G.E. Hall et al., Isolation and Characterization of Nuclear Scaffolds, *In: Plant Molecular Biology* (2d Ed.), Stanton, Gelvin and Schilperoort (Eds.); Kluwer Academic Publishers (1994).
Y.T. Yamamoto et al., Root–specific Genes from Tobacco and Arabidopsis Homologous to an Evolutionarily conserved Gene Family of Membrane Channel Proteins, *Nucleic Acids Research* 18:7449 (1990).
Y.T. Yamamoto et al., Characterization of cis–acting Sequences Regulating Root–specific Gene Expression in Tobacco, *The Plant Cell* 3:371–382 (1991).

*Primary Examiner*—David Guzo
*Assistant Examiner*—Irem Yurel
*Attorney, Agent, or Firm*—Myers Bigel Sibley & Sajovec, P.A.

[57] ABSTRACT

A nuclear scaffold attachment region isolated from a tobacco gene, and a method of making recombinant cells having increased levels of expression of foreign genes therein, are described. The method comprises transforming the cell with a DNA construct comprising in the 5' to 3' direction, a transcription initiation region, a structural gene positioned downstream from the transcription initiation region and operatively associated therewith, and a scaffold attachment region of the nucleotide sequence provided herein, positioned either 5' to the transcription initiation region or 3' to the structural gene. DNA constructs and vectors employed in carrying out the foregoing method are also discussed.

28 Claims, 3 Drawing Sheets

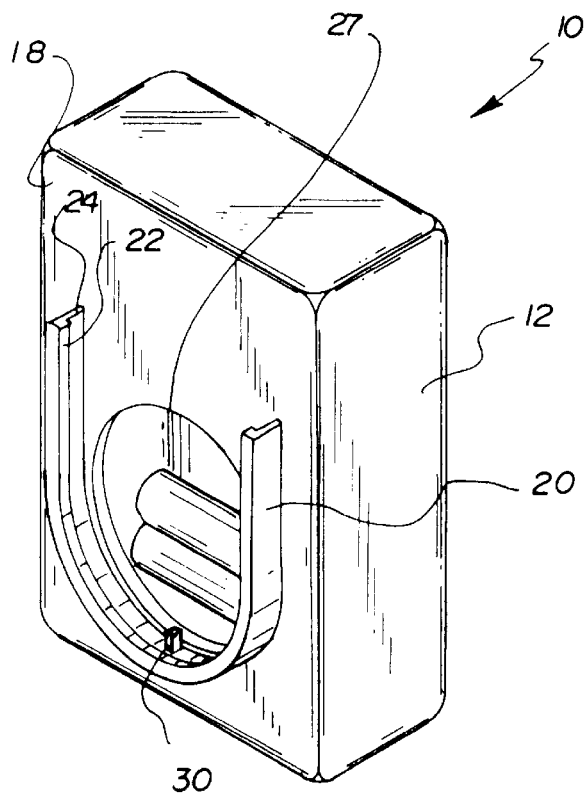
IFig. 1
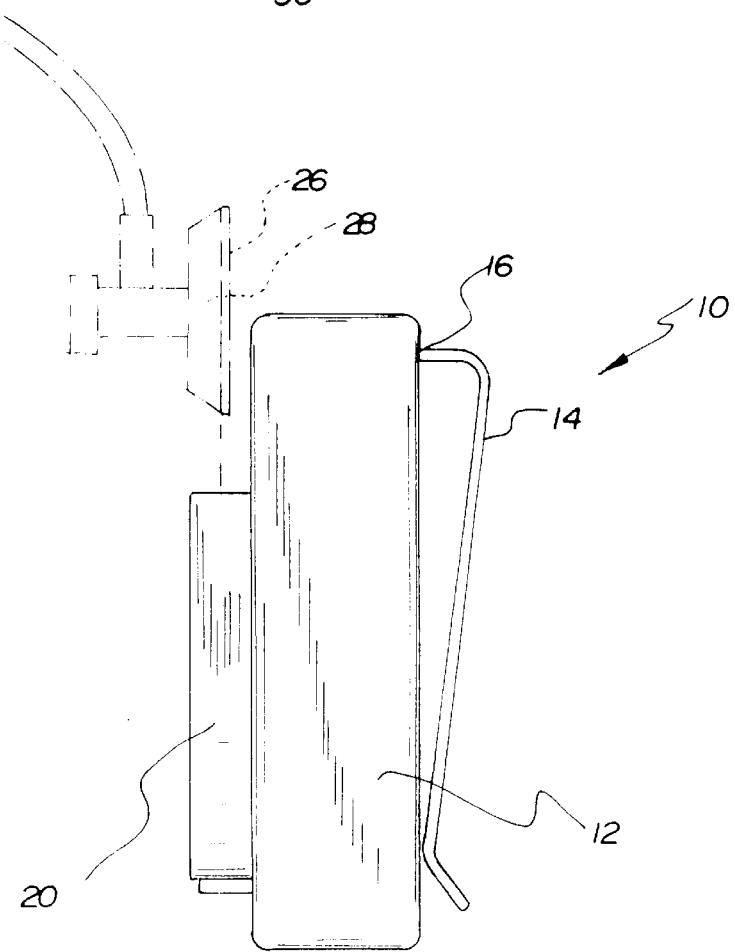
IFig. 2

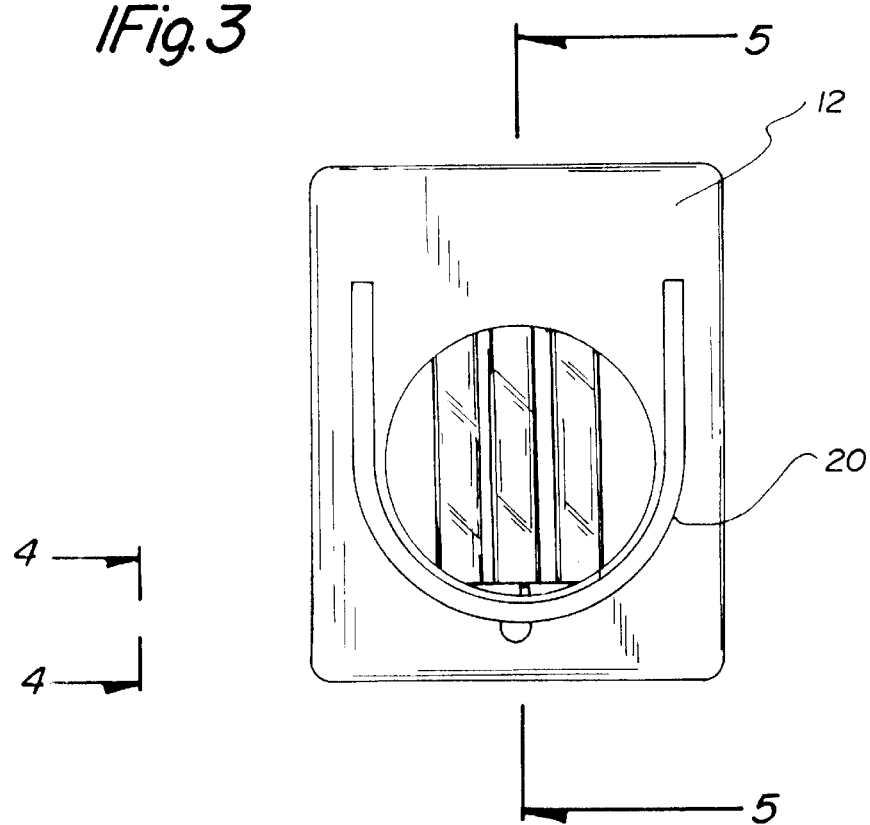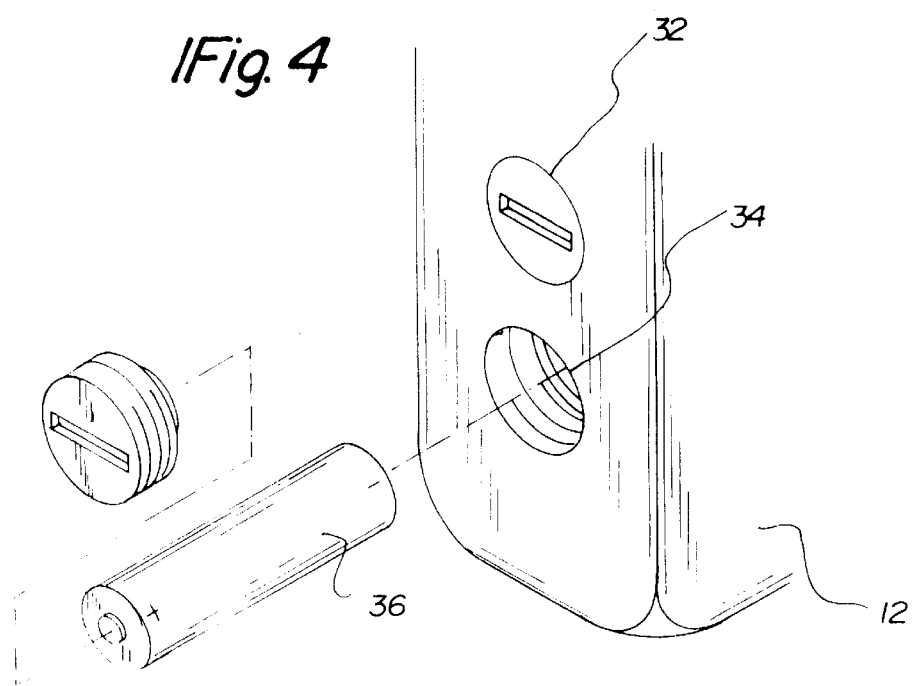

5,773,695

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1167 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CGATTAAAAA  TCCCAATTAT  ATTTGGTCTA  ATTTAGTTTG  GTATTGAGTA  AAACAAATTC        60

GAACCAAACC  AAAATATAAA  TATATAGTTT  TTATATATAT  GCCTTTAAGA  CTTTTTATAG       120

AATTTTCTTT  AAAAAATATC  TAGAAATATT  TGCGACTCTT  CTGGCATGTA  ATATTTCGTT       180

AAATATGAAG  TGCTCCATTT  TTATTAACTT  TAAATAATTG  GTTGTACGAT  CACTTTCTTA       240

TCAAGTGTTA  CTAAAATGCG  TCAATCTCTT  TGTTCTTCCA  TATTCATATG  TCAAAATCTA       300

TCAAAATTCT  TATATATCTT  TTTCGAATTT  GAAGTGAAAT  TTCGATAATT  TAAAATTAAA       360
```

-continued

| | | | | | |
|---|---|---|---|---|---|
| TAGAACATAT | CATTATTTAG | GTATCATATT | GATTTTTATA | CTTAATTACT | AAATTTGGTT | 420 |
| AACTTTGAAA | GTGTACATCA | ACGAAAAATT | AGTCAAACGA | CTAAAATAAA | TAAATATCAT | 480 |
| GTGTTATTAA | GAAAATTCTC | CTATAAGAAT | ATTTAATAG | ATCATATGTT | TGTAAAAAAA | 540 |
| ATTAATTTTT | ACTAACACAT | ATATTTACTT | ATCAAAAATT | TGACAAAGTA | AGATTAAAAT | 600 |
| AATATTCATC | TAACAAAAAA | AAAACCAGAA | AATGCTGAAA | ACCCGGCAAA | ACCGAACCAA | 660 |
| TCCAAACCGA | TATAGTTGGT | TTGGTTTGAT | TTTGATATAA | ACCGAACCAA | CTCGGTCCAT | 720 |
| TTGCACCCCT | AATCATAATA | GCTTTAATAT | TTCAAGATAT | TATTAAGTTA | ACGTTGTCAA | 780 |
| TATCCTGGAA | ATTTTGCAAA | ATGAATCAAG | CCTATATGGC | TGTAATATGA | ATTTAAAAGC | 840 |
| AGCTCGATGT | GGTGGTAATA | TGTAATTTAC | TTGATTCTAA | AAAAATATCC | CAAGTATTAA | 900 |
| TAATTTCTGC | TAGGAAGAAG | GTTAGCTACG | ATTTACAGCA | AAGCCAGAAT | ACAAAGAACC | 960 |
| ATAAAGTGAT | TGAAGCTCGA | AATATACGAA | GGAACAAATA | TTTTTAAAAA | AATACGCAAT | 1020 |
| GACTTGGAAC | AAAAGAAAGT | GATATATTTT | TTGTTCTTAA | ACAAGCATCC | CCTCTAAAGA | 1080 |
| ATGGCAGTTT | TCCTTTGCAT | GTAACTATTA | TGCTCCCTTC | GTTACAAAAA | TTTTGGACTA | 1140 |
| CTATTGGGAA | CTTCTTCTGA | AAATAGT | | | | 1167 |

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

TCAAGATGCC TCTGCCGACA                                                                 20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCACGGGTTG GGGTTTCTAC                                                                 20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGAACTGACA GAACCGCAAC                                                                 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:5:

GGACAGGTCG GTCTTGACAA                                                                                              20

PLANT NUCLEAR SCAFFOLD ATTACHMENT REGION AND METHOD FOR INCREASING GENE EXPRESSION IN TRANSGENIC CELLS

This invention was made with Government support under USDA research grants #91-37301-6377 and 92-37301-7710. The Government may have certain rights to this invention.

FIELD OF THE INVENTION

The present invention relates to a plant nuclear scaffold attachment region and to methods for increasing the expression of foreign genes in cells, along with DNA constructs for carrying out such methods.

BACKGROUND OF THE INVENTION

The proteinaceous nuclear 'matrix' or 'scaffold' of cells plays a role in determining chromatin structure. Electron micrographs show that nuclear DNA is attached to this scaffold at intervals to produce a series of loops (Zlatanova and Van Holde, *J. Cell Sci.* 103:889 (1992)). Scaffold Attachment Regions (SARs) are AT-rich genomic DNA sequences which bind specifically to components of the nuclear scaffold. See Boulikas, *J. Cell. Biochem.* 52:14 (1993). These sequences are thought to define independent chromatin domains through their attachment to the nuclear scaffold. Both transcription and replication are thought to occur at the nuclear scaffold.

It has been shown that when SARs are included on both sides of a transgene the expression level in stably transfected cell lines may become proportional to transgene copy number, indicating that gene activity is independent of position in the chromosome (Bonifer et al., *EMBO J.* 9:2843 (1990); McKnight et al., *Proc. Natl. Acad. Sci. USA* 89:6943 (1992); Phi-Van et al., *Mol. Cell. Biol.* 10:2303 (1990)). Flanking a GUS reporter gene with yeast SARs has been reported to result in higher and less variable transgene expression in plant cells. Allen et al. Plant Cell 5:603 (1993). However, variation between different transformants was not dramatically reduced, and high levels of expression were not seen in transformants containing many copies of the transgene.

SUMMARY OF THE INVENTION

In view of the foregoing, a first aspect of the present invention is an isolated DNA molecule having a nucleotide sequence of SEQ ID NO:1.

A further aspect of the present invention is a DNA construct comprising a transcription initiation region, a structural gene, and a scaffold attachment region of SEQ ID NO:1.

Further aspects of the present invention are transformed plant cells containing a DNA construct as described above, and recombinant plants comprising such transformed plant cells.

A further aspect of the present invention is a method of making transgenic plant cells with increased expression of foreign genes. The method includes transforming a plant cell capable of regeneration with a DNA construct of the present invention.

A further aspect of the present invention is a method of making recombinant tobacco plant cells having increased expression of foreign genes. The method includes transforming a tobacco plant cell with a DNA construct according to the present invention.

A further aspect of the present invention is a plant transformation vector carrying a DNA construct which includes a transcription initiation region, a structural gene, and a scaffold attachment region of SEQ ID NO:1.

DETAILED DESCRIPTION OF THE INVENTION

Figure 5:
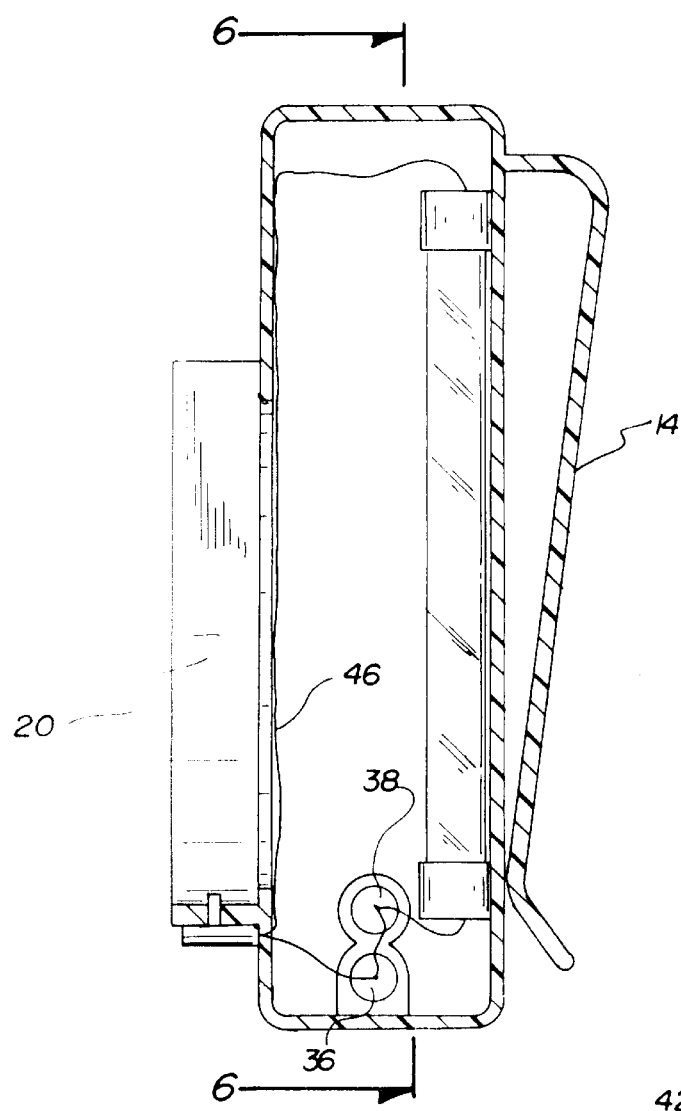
FIG. 5 is a plot of NPT protein against gene copy number, where open squares represent RB7 SAR(+) transformants and closed triangles represent control lines.

The present inventors have found that a SAR (RB7 SAR) isolated from tobacco (SEQ ID NO:1) used in conjunction with a transgene can increase average expression per gene copy by more than 100-fold in stably transformed cell lines.

The present tobacco SAR effect was found to be maximal at relatively low transgene copy numbers.

The loop domain model of chromatin organization predicts that SARs act as boundary elements, limiting the spread of condensed chromatin structures and blocking the influence of cis-regulatory elements in neighboring chromatin. Thus, if variation in transgene expression is mainly attributable to genomic position effects, the presence of flanking SARs should normalize expression per gene copy and substantially reduce variability among independent transformants. Total gene expression should then vary in direct proportion to gene copy number. Experiments with animal cell systems have supported this prediction. Grosveld et al. *Cell* 51:975 (1987); Stief et al. *Nature* 341:343 (1989); Bonifer et al., *EMBO J.* 9:2843 (1990); McKnight et al., *Proc. Natl. Acad. Sci. USA* 89:6943 (1992); Phi-Van et al., *Mol. Cell. Biol.* 10:2303 (1990).

Recent evidence indicates that one or more 'gene silencing' phenomena also contribute to overall variability, especially in fungal and higher plant systems. Assaad et al., *Plant Mol. Biol.* 22:1067 (1993); Finnegan and McElroy, *Bio/Technology* 12:883 (1994); Flavell, *Proc. Natl. Acad. Sci USA* 91:3490 (1994). In principle, position effects on transgene expression reflect pre-existing features of the insertion site, such as proximity to genomic enhancers and degree of chromatin condensation, while gene silencing results from homology-dependent interactions involving the transgene itself, although chromosomal location may influence the severity of these interactions.

While not wishing to be held to a single theory, the present inventors propose that a portion of the large SAR effects seen with the SAR of the present invention reflect a reduction in the severity of gene silencing under conditions in which control transformants are severely affected. Homology-dependent gene silencing must be considered whenever multiple transgenes are present. Although best known in fungi and higher plants, silencing of multicopy insertions has recently been reported in Drosophila as well (Dorer and Henikoff, *Cell* 77:993 (1994)).

The predominance of multicopy insertions in the transformants reported herein may be one reason the presently reported RB7 SAR effects vary from those reported by laboratories using Agrobacterium vectors for transformation. In four reports, a moderate increase in expression was reported along with a decrease in variation between transformants (Mlynarova et al., *Plant Cell* 7:599 (1995); Mlynarova et al, *Plant Cell* 6:417 (1994); Schoffl et al., *Transgenic Res.* 2:93 (1993); van der Geest et al, *Plant J.* 6:413 (1994)). Breyne et al., *Plant Cell* 4:463 (1992) reported a decrease in average gene expression. Direct DNA-mediated transformation frequently produces complex loci in which multiple transgene copies are integrated at a single genomic site. Interactions among homologous sequences at a single locus are thought to increase the frequency of silencing, thus it would be expected that the transformants reported in the Examples wherein would be more affected by silencing than those obtained with Agrobacterium vectors that only occasionally produce multicopy events.

The present invention may be used to transform cells from a variety of organisms, including plants (i.e., vascular plants). As used herein, plants includes both gymnosperms and angiosperms (i.e., monocots and dicots). Transformation according to the present invention may be used to increase expression levels of transgenes in stably transformed cells.

The term "operatively associated," as used herein, refers to DNA sequences on a single DNA molecule which are associated so that the function of one is affected by the other. Thus, a transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

DNA constructs, or "expression cassettes," of the present invention preferably include, 5' to 3' in the direction of transcription, a first scaffold attachment region, a transcription initiation region, a structural gene operatively associated with the transcription initiation region, a termination sequence including a stop signal for RNA polymerase and a polyadenylation signal for polyadenylation (e.g., the nos terminator), and a second scaffold attachment region. All of these regions should be capable of operating in the cells to be transformed. The termination region may be derived from the same gene as the transcription initiation or promoter region, or may be derived from a different gene.

The scaffold attachment regions (or "SARs") used to carry out the present invention have the nucleotide sequence of SEQ ID NO: 1 provided herein (RB7 SAR). The RB7 SAR may be isolated from natural sources or may be chemically synthesized.

SARs are known to act in an orientation-independent manner. Poljak et al., *Nucleic Acids Res.* 22:4386 (1994). Genetic constructs of the present invention may contain RB7 SARs oriented as direct repeats in a single orientation (→→), direct repeats in the opposite orientation (←←), or either of two possible indirect repeats (→← or ←→).

The transcription initiation region, which preferably includes the RNA polymerase binding site (promoter), may be native to the host organism to be transformed or may be derived from an alternative source, where the region is functional in the host. Other sources include the Agrobacterium T-DNA genes, such as the transcriptional initiation regions for the biosynthesis of nopaline, octapine, mannopine, or other opine transcriptional initiation regions, transcriptional initiation regions from plants, transcriptional initiation regions from viruses (including host specific viruses), or partially or wholly synthetic transcription initiation regions. Transcriptional initiation and termination regions are well known. See, e.g., dGreve, *J. Mol. Appl. Genet.* 1, 499–511 (1983); Salomon et al., *EMBO J.* 3, 141–146 (1984); Garfinkel et al., *Cell* 27, 143–153 (1983); and Barker et al., *Plant Mol. Biol.* 2, 235–350 (1983).

The transcriptional initiation regions may, in addition to the RNA polymerase binding site, include regions which regulate transcription, where the regulation involves, for example, chemical or physical repression or induction (e.g., regulation based on metabolites or light) or regulation based on cell differentiation (such as associated with leaves, roots, seed, or the like in plants). Thus, the transcriptional initiation region, or the regulatory portion of such region, is obtained from an appropriate gene which is so regulated. For example, the 1,5-ribulose biphosphate carboxylase gene is light-induced and may be used for transcriptional initiation. Other genes are known which are induced by stress, temperature, wounding, pathogen effects, etc.

Structural genes are those portions of genes which comprise a DNA segment coding for a protein, polypeptide, or portion thereof, possibly including a ribosome binding site and/or a translational start codon, but lacking a transcription initiation region. The term can also refer to introduced copies of a structural gene where that gene is also naturally found within the cell being transformed. The structural gene may encode a protein not normally found in the cell in which the gene is introduced or in combination with the transcription initiation region to which it is operationally associated, in which case it is termed a heterologous structural gene. Genes which may be operationally associated with a transcription initiation region of the present invention for expression in a plant species may be derived from a chromosomal gene, cDNA, a synthetic gene, or combinations thereof. Any structural gene may be employed. Where plant cells are transformed, the structural gene may encode an enzyme to introduce a desired trait, such as glyphosphate resistance; a protein such as a *Bacillus thuringiensis* protein (or fragment thereof) to impart insect resistance; or a plant virus protein or fragment thereof to impart virus resistance.

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly a plant host. The markers may be protection against a biocide, such as antibiotics, toxins, heavy metals, or the like; provide complementation, for example by imparting prototrophy to an auxotrophic host; or provide a visible phenotype through the production of a novel compound. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production, luciferase, providing visible light production, NPTII, providing kanamycin resistance or G418 resistance, HPT, providing hygromycin resistance, and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Sambrook et al., Molecular Cloning: A Laboratory Manual, (2d Ed. 1989)(Cold Spring Harbor Laboratory, Cold Spring Harbor, N.Y.).

Vectors which may be used to transform plant tissue with DNA constructs of the present invention include non-Agrobacterium vectors, particularly ballistic vectors, as well as vectors suitable for DNA-mediated transformation.

Microparticles carrying a DNA construct of the present invention, which microparticles are suitable for the ballistic transformation of a cell, are also useful for transforming cells according to the present invention. The microparticle is propelled into a cell to produce a transformed cell. Where the transformed cell is a plant cell, a plant may be regenerated from the transformed cell according to techniques known in the art. Any suitable ballistic cell transformation methodology and apparatus can be used in practicing the present invention. Exemplary apparatus and procedures are disclosed in Stomp et al., U.S. Pat. No. 5,122,466; and Sanford and Wolf, U.S. Pat. No. 4,945,050 (the disclosures of all U.S. Patent references cited herein are incorporated herein by reference in their entirety). When using ballistic transformation procedures, the expression cassette may be incorporated into a plasmid capable of replicating in the cell to be transformed. Examples of microparticles suitable for use in such systems include 1 to 5 µm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or Ti) transformed plants may be selfed to give homozygous second generation (or T2) transformed plants, and the T2 plants further propagated through classical breeding techniques. A dominant selectable marker (such as npt II) can be associated with the expression cassette to assist in breeding.

Plants which may be employed in practicing the present invention include (but are not limited to) tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassava (*Manihot esculenta*), coffee (*Cofea spp.*), coconut (*Cocos nucifera*), pineapple (*Ananas comosus*), citrus trees (*Citrus spp.*), cocoa (*Theobroma cacao*), tea (*Camellia sinensis*), banana (*Musa spp.*), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), lettuce (*e.g., Lactuea* sativa), green beans (*Phaseolus vulgaris*), lima beans (*Phaseolus limensis*), peas (*Pisum spp.*) and members of the genus Cucumis such as cucumber (*C. sativus*), cantaloupe (*C. cantalupensis*), and musk melon (*C. melo*). Ornamentals include azalea (*Rhododendron spp.*), hydrangea (*Macrophylla hydrangea*), hibiscus (*Hibiscus rosasanensis*), roses (*Rosa spp.*), tulips (*Tulipa spp.*), daffodils (*Narcissus spp.*), petunias (*Petunia hybrida*), carnation (*dianthus caryophyllus*), poinsettia (*Euphorbia pulcherima*), and chrysanthemum. Gymnosperms which may be employed to carrying out the present invention include conifers, including pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The examples which follow are set forth to illustrate the present invention, and are not to be construed as limiting thereof.

EXAMPLE 1

Methods
1. Plasmid Constructs

A GUS reporter plasmid was made by using a Klenow filled-in blunt-ended 1.1 kb ClaI/ScaI SAR fragment (SEQ ID NO:1) from pRB7-6 (Hall et al., *Proc. Natl. Acad. Sci. USA* 88:9320 (1991)), which was inserted into Klenow filled-in blunt-ended XbaI site in pBluescript II SK+ (Stratagene), resulting in plasmid pGHNC1. Similarly, the 1.1 kb ClaI/ScaI SAR fragment (SE (SEQ ID NO:1) was also inserted into the Klenow filled-in blunt-ended XhoI site in pBluescript II SK+ (Stratagene) resulting in pGHNC4. The 1.1 kb ApaI/HindIII fragment from pGHNC4 was then inserted into the ApaI/HindIII sites of pGHNC1 to give pGHNC5. The 2.8 kb HindIII/EcoRI fragment from pBI221 (Clonetech), containing the 35S promoter/GUS reading frame/Nos terminator, was inserted into the HindIII/EcoRI sites of pGHNC5 or pBluescript II SK+ to yield pGHNC11 (+SARs) or pGHNC12 (−SARs), respectively.

The selection plasmid (pGHNC10) was created by ligating the HindIII/EcoRI fragment containing the nos promoter/NPT II reading frame/Ocs terminator from pUCNK1 (Herrera-Estrella et al., IN: Gelvin et al. (Eds.), Plant Molecular Biology Manual, Kluwer Academic Publishers, Dordrecht, The Netherlands, pp. 1–22 (1988)) into the Hind III/EcoRI sites of pBluescript II SK+.

2. Transformation

The *Nicotiana tabacum* cell line NT-1 was obtained from G. An, Washington State University. Suspension cultures were grown in a medium containing Murashige and Skoog salts (GIBCO Laboratories, Grand Island, N.Y.) supplemented with 100 mg/L inositol, 1 mg/L thiamine HC1, 180 mg/L $KH_2PO_4$, 30 g/L sucrose, and 2 mg/L 2,4-dichlorophenoxyacetic acid. The pH was adjusted to 5.7 before autoclaving. Cells were subcultured once per week by adding 3 ml of inoculum to 100 ml of fresh medium in 500 ml Erlenmeyer flasks. The flasks were placed on a rotary shaker at 125 rpm and 27° C. with a light intensity of 47 $\mu$mol $m^{-2} sec^{-1}$.

Four-day-old cells, in early log phase, were transformed by microprojectile bombardment. Aliquots of 50 ml were centrifuged and the pellet resuspended in fresh culture medium at a concentration of 0.1 g/ml. Aliquots of 0.5 ml were spread as monolayers onto sterile lens paper which had been placed on culture medium solidified with 0.8% agar in 60 mm petri plates. Plated cells were kept at 23° C. for 3 h prior to bombardment. Microprojectile bombardment was carried out with a DuPont PDS-1000 Particle Accelerator using a normal rupture disk valve of 1500 psi with the sample positioned 5.5 cm from the launch assembly.

Each batch of cells was co-transformed with a mixture of "expression" and "selection" plasmids. A β-glucuronidase (GUS) gene driven by the CaMV 35S promoter (Benfey and Chua, *Science* 244:174 (1989)) was used to measure expression, while a neomycin phosphotransferase gene (nptII) driven by the nopaline synthase promoter (Depicker et al., 1982) was used to select for cells which had stably integrated exogenous DNA. All plasmids were amplified in *Escherichia coli* strain DH5α and isolated using a Quiagen plasmid maxiprep kit (Quiagen, Inc. Chatsworth, Calif.). Co-transformation mixtures contained a 4:1 molar ratio of GUS reporter plasmid to nptII selection plasmid. Therefore, each 500 ng SAR transformation mixture consisted of 432 ng pGHNC11 and 68 ng pGHNC10, whereas control mixtures contained 314 ng pGHNC12 and 68 ng pGHNC10. Each DNA preparation (in 5 $\mu$L TE buffer) was mixed and precipitated with 50 $\mu$L of 2.5M $CaCl_2$ and 20 $\mu$L of 0.1M spermidine onto 1.0 $\mu$m gold microprojectiles.

After bombardment, the petri plates were sealed with parafilm and incubated for 24 h at 27° C. under constant light. Using the lens paper, cells were then transferred to fresh plates containing medium supplemented with 100 $\mu$g per ml kanamycin. Isolated kanamycin resistant microcalli began to appear in approximately 3 weeks, at which time they were transferred to fresh plates containing kanamycin medium. After 1 week's growth on plates, a suspension culture was started for each callus by inoculating 1 ml broth supplemented with 50 $\mu$g kanamycin per ml. Once established, the suspension cultures were transferred weekly using 3% (v/v) inocula in 5 ml broth supplemented with 50 $\mu$g per ml kanamycin.

3. Gene Copy Number Analysis

DNA was isolated as previously described (Allen et al., *Plant Cell* 5:603 (1993)). Estimates of GUS and nptII gene copy number were obtained for all cell lines by quantitative polymerase chain reaction (PCR) procedure, and confirmed for representative lines by genomic Southern analysis. The PCR procedure for GUS gene copy number analysis used primers located in the CaMV35S promoter (5'-TCAAGATGCC TCTGCCGACA-3') (SEQ ID NO:2) and in the translated region of the GUS gene (5'-TCACGGGTTG GGGTTTCTAC-3') (SEQ ID NO:3) and for nptII gene copy analysis used primers located in the nos promoter (5'-GGAACTGACA GAACCGCAAC-3') (SEQ ID NO:4) and in the translated region of the nptII gene (5'-GGACAGGTCG GTCTTGACAA-3') (SEQ ID NO:5). A Hot Start PCR procedure using Ampli Wax beads (Perkin Elmer) was used according to the manufacturer's instructions. The lower reaction mixture (25 $\mu$L) contained 0.8 mM dNTPs, 6 mM $MgCl_2$, 0.4 mM of each oligonucleotide primer, 50 mM KC1, 10 mM Tris-HC1 (pH 8.8). The upper reaction mixture (75 $\mu$l) contained 50 mM KC1, 10 mM Tris-HC1 (pH 8.8), 2.5 U Taq Polymerase, and 100 ng genomic DNA in 10 $\mu$l TE. Each cycle consisted of 2 min at 94° C., 2.5 min at 50° C., and 3 min at 72° C. Reactions were terminated following a final extension step of 7 min at 72° C.

PCR was limited to eighteen cycles for both the GUS and nptII copy number analysis to avoid substrate exhaustion, and amplification products were visualized by blotting and hybridization with $^{32}$P-labeled DNA probe. Reconstruction standards were prepared by serially diluting DNA from the pGHNC11 (+SARs) into wild-type NT-1 genomic DNA so as to introduce between 1 and 150 GUS genes per 1 C (5 pg) equivalent of tobacco DNA (Arumuganathan and Earle, 1991). PCR reactions were done simultaneously for standards and unknowns. Similarly, the nptII reconstruction standards were prepared by serially diluting DNA from the pGHNC10 into wild-type NT-1 genomic DNA so as to introduce between 1 and 40 nptII genes per 1 C. Hybridization signals were quantified on an Ambis radioanalytical scanner (Ambis, San Diego, Calif.), and a final copy number estimates were calculated using linear regression analysis.

4. DNA Gel Blot Analysis

Southern analysis was done as described by Murray et al. *Plant Mol. Biol. Rep.* 10:173 (1992). Agarose gels were stained with 0.5 mg/ml ethidium bromide and photographed. The top ⅓ of the gels were treated with 0.25N HCl for 10 minutes. The gels were then incubated twice for 15 minutes in 150 mM NaOH 3 mM EDTA, and twice for 15 minutes in 150 mM NaPO$_4$ pH 7.4, and blotted to Genescreen Plus (New England Nuclear) by the method of Southern (Sambrook et al., Molecular Cloning: A Laboratory Manual, (2d Ed. 1989) Cold Spring Harbor Laboratory, Cold Spring Harbor, N.Y.).1989) using 25 mM sodium pyrophosphate. The membranes were blocked by incubating in 2% SDS, 0.5% BSA, 1 mM EDTA, 1 mM 1,10-phenanthroline and hybridized in 100 mM NaPO$_4$ pH 7.8, 20 mM Na pyrophosphate, 5 mM EDTA, 1 mM 1,10-phenanthroline, 0.1% SDS, 10% dextran sulfate, 500 μg/ml heparin sulfate, 50 μg/ml yeast RNA, 50 μg/ml herring sperm DNA. Probes were prepared with the Random Prime DNA Labeling kit from United States Biochemical Co. washing conditions included one wash at room temperature with 2X SSC, 0.5% SDS for 5 minutes, one wash at room temperature with 2X SSC, 0.1% SDS for 15 minutes, two washes at room temperature with 0.1 X SSC, 0.5% SDS for 15 minutes, and two washes at 37° C. with 0.1 X SSC, 0.5% SDS for 30 minutes.

5. NPTII and GUS assays

For NPTII protein assays cells were ground in liquid nitrogen and suspended in 100 μl of 0.25M TrisCl, pH 7.8. The mixture was centrifuged and the supernatant was used for ELISA analysis using an NPTII ELISA kit (5'→3') according to the instructions of the manufacturer.

For GUS fluorometric analysis, frozen cells were ground in liquid nitrogen as described for the NPTII and DNA extraction. Approximately 50 mg of the resulting powder was resuspended in 600 μl of GUS extraction buffer containing 50 mM NaPO$_4$, pH 7.0, 10 mM β-mercaptoethanol, 10 mM Na$_2$EDTA, 0.1% sodium lauryl sarcosine (w/v), and 0.1% Triton X-100 (w/v) and sonicated twice for 10 sec. The extract was clarified by treatment with insoluble polyvinyl polypyrrolidone and centrifuged. GUS activity was determined by means of the fluorometric assay described by Jefferson, *Plant Mol. Biol. Rep.* 5:387 (1987); Jefferson et al., *EMBO J.* 6:3901 (1987), using methylumbelliferone glucuronide (MUG) as substrate. Total protein was measured using the BioRad Protein assay kit (BioRad Laboratories, Melville, N.Y.) and GUS specific activity reported as nmols 4-methyl umbelliferone (4-MU) formed ●min$^{-1}$●mg protein$^{-1}$ from the initial velocity of the reaction.

6. Transient Expression

Protoplasts for electroporation were prepared from 4-day-old NT-1 suspension cultures by a procedure similar to that of Hall et al., *Proc. Natl. Acad. Sci. USA* 88:9320 (1991). Cells from 100 ml of culture were harvested by centrifugation (300×g for 2 min), washed twice in 100 ml of 0.4M mannitol, and resuspended in an equal volume of protoplasting solution containing 0.4M mannitol, 20 mM MES, pH 5.5, 1% cellulase (Onozuka RS) and 0.1% pectolyase Y23 (Onozuka). They were then incubated at 25° C. for 30–60 min with shaking at 150 rpm. The resulting protoplasts were washed twice in protoplast buffer containing 0.4M mannitol by centrifuging at 300×g for 5 min in a Beckman GPR centrifuge equipped with GH3.7 rotor. A protoplast concentration of 4×10$^6$ per ml was obtained by diluting the mixture with 0.4M mannitol. The resulting suspension was then diluted by adding an equal volume of 2X electroporation buffer to a final concentration of 2×10$^6$ protoplasts per ml. The 2X electroporation buffer contained 273 mM NaCl, 5.36 mM KCl, 2.94 mM KH$_2$PO$_4$, 15.5 mM Na$_2$HPO$_4$, 0.4M mannitol, pH 6.5.

Each electroporation used 80 μg sheared *E.coli* carrier DNA and 20 μg of the plasmid DNA mixture to be tested. One ml of protoplast was added to the electroporation cuvette (BRL), mixed with 100 μL DNA mixture in TE buffer, and left on ice for 5 min. Electroporation was done in a BRL Cell-Porator at 250 V and 1180 μF. Cuvettes were placed on ice for 15 min immediately after treatment. Aliquots (400 μl) of electroporated protoplasts were then transferred to 60 mm Petri plates containing 4 ml of culture medium with 0.4M mannitol. After incubation for various time periods, protoplasts were collected by centrifugation at 300×g for 5 min. at 4° C. Each pellet was suspended in 600 μl GUS extraction buffer, and GUS activity was assayed by the fluorogenic procedure described above.

7. Isolation of Plant Nuclear Scaffold and Binding Assays

Nuclei and nuclear scaffolds from NT-1 cells were isolated as previously described (Hall et al., *Proc. Natl. Acad. Sci. USA* 88:9320 (1991); Hall and Spiker, IN: Gelvin et al. (Eds), Plant Molecular Biology Manual, Kluwer Academic Publishers, Dordrecht, pp. 1–12 (1994)). The resulting nuclear halos were washed 2 times with Digestion/Binding Buffer (D/BB, pH 6.5) which contains 70 mM NaCl; 20 mM Tris, pH 8.0; 20 mM KCl; 0.1% digitonin; 1% thiodiglycol; 50 mM spermine; 125 mM spermidine with 0.5 mM PMSF and 2 μg ml$^{-1}$ aprotinin (Hall et al., 1991; Hall and Spiker, 1994). The halos were then washed again in the same buffer containing 10 mM MgCl$_2$. The halos were then diluted to 4×10$^6$ ml$^{-1}$ in D/BB containing 0.5 mM PMSF; 2 μg ml$^{-1}$ aprotinin; 10 mM phenanthroline; and 10 mM MgCl$_2$; and digested with 500 units ml$^{-1}$ of the various restriction enzymes (New England Biolabs) at 37° C. for 1 h. Fresh enzymes were then added and the incubation was continued for an additional 1 h. Aliquots (100 μl) containing scaffolds representing approximately 8×10$^5$ nuclei were centrifuged at 2600×g, the supernatant was removed, and the scaffold pellets resuspended in D/BB containing 0.5 mM PMSF; 2 μg ml$^{-1}$ aprotinin, and 10 mM MgCl$_2$.

For binding assays, four μmoles of $^{32}$p end-labeled fragments previously digested with restriction enzymes (New England Biolabs), were added to the 100 μl scaffold aliquot along with appropriate competitor DNA and incubated at 37° C. for 3 h with frequent mixings. The scaffold aliquots were centrifuged at 2600×g and the pellet (containing scaffold-bound DNA fragments) and the supernatant containing non-binding fragments were separated. The pellet fraction was washed in 200 μl of D/BB with 10 mM MgCl$_2$, resuspended in 100 μl TE buffer (representing 100%) containing 0.5% SDS with 0.5 mg ml$^{-1}$ proteinase K, and incubated at room temperature overnight. Equal fractions (usually 20%) of pellet and supernatant fractions were separated on a 1% agarose gel in TAE buffer (Sambrook et al., 1989). The gel was treated with 7% trichloroacetic acid for 20 min and dried onto filter paper followed by exposure to X-ray film.

EXAMPLE 2
SAR Motifs and Predicted Scaffold Binding Activity

Figure 1:
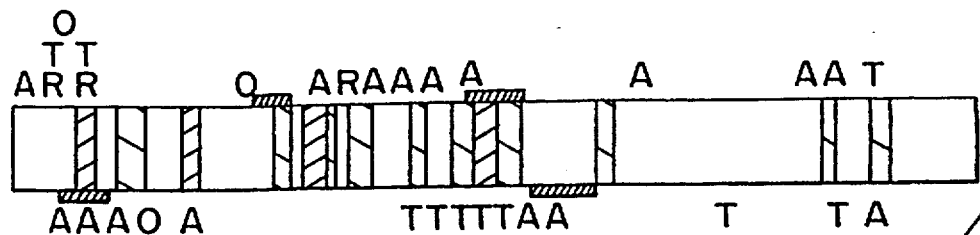
FIG. 1 provides a schematic comparison of SAR sequence motifs in the 1167 base pair tobacco SAR (RB7 SAR) of the present invention (SEQ ID NO:1) and the 838 base pair yeast SAR (ARS-1), showing A boxes (A), T boxes (T), Drosophila topoisomerase II sites (O), ARS consensus sequences (R), and G exclusion regions (ATC tract of 30 bp) represented by the black side bars. Local AT-rich regions (>20 bp) are indicated by the dark hatched boxes (regions of 95% AT) or lighter hatched boxes (90–95% AT).
Figure 1:
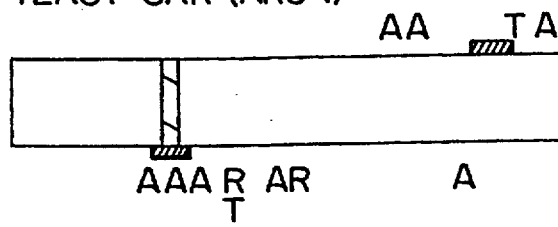

SARs are highly variable in sequence, however, several loosely defined SAR-related consensus elements or motifs have been identified from sequence comparisons in yeast and animal systems (Dickinson et al., Cell 70:631 (1992); Gasser et al., Int. Rev. Cytol. 119:57 (1989); Gasser and Laemmli, EMBO J. 5:511 (1986); Mielke et al., Biochem. 29:7475 (1990)). FIG. 1 shows the distribution of some of these motifs in the 1186 base pair tobacco RB7 SAR (SEQ ID NO:1), and in an 838 base pair yeast SAR sequence (ARS-1, Allen et al., Plant Cell 5:603 (1993)).

In FIG. 1, A boxes (A) were scored as an 8/10 or better match with the consensus sequence AATAAAYAAA, where Y=pyrimidine. T boxes (T) were scored as a 9/10 or better match with the consensus TTWTWTTWTT, where W=A or T. Drosophila topoisomerase II sites (O) were scored as a 13/15 or better match with the consensus GTNWAYATTN ATNNG. ARS consensus sequences (WTTTATATTTW) are indicated by (R). G exclusion regions (ATC tracts of 30 base pairs) are represented by black side bars. Local AT-rich regions (>20 bp) are indicated by the dark hatched boxes (regions of 95% AT) or lighter hatched boxes (90–95% AT).

The yeast SAR contains several A boxes and T boxes. In addition, there is one ARS consensus element, two G-exclusion regions or ATC tracts of 30 bp, and a 20 bp tract containing 90% A+T. The plant SAR (SEQ ID NO:1) contains a much higher density of A and T box motifs, A-Trich tracts, and G-exclusion regions, as well as three elements with homology to the Drosophila topoisomerase II consensus sequence. A systematic study of randomly cloned plant SARs (unpublished data) has not revealed a close correlation between any one of these motifs and binding activity in an in vitro assay. However, binding activity does correlate loosely with the total number or overall density of SAR-related motifs. From this analysis and the data summarized in FIG. 1, it was predicted that a SAR of SEQ ID NO:1 should bind to scaffold preparations much more strongly than the yeast SAR (ARS-1).

EXAMPLE 3
Scaffold Binding Activity

The RB7 SAR (SEQ ID NO:1) consistently showed a The binding activity of the tobacco RB7 SAR (SEQ ID NO:1) was compared to that of the ARS-1 SAR. End-labeled restriction fragments from plasmids containing the SAR sequences to be tested were mixed with tobacco nuclear scaffold preparations in the presence of restricted plant genomic DNA as nonspecific competitor. Plasmid pGA-1 contained the yeast SAR (ARS-1) and TRP1, and was digested with EcoRI and HINDIII. Plasmid pB7-6 Sca/Cla contained the RB7 tobacco SAR of SEQ ID NO:1, and was digested with SpeI and XhoI. After incubation with tobacco nuclear scaffold preparations under binding conditions, bound and unbound DNA fragments were separated by centrifugation, and DNA was purified prior to gel analysis.

Equal percentages (20%) of the pellet and supernatant from each reaction using plasmid pGA-1, as well as an equivalent aliquot of the unfractionated probe, were run on adjacent lanes of an agarose gel and visualized by autoradiography (results not shown). This same procedure was replicated using a 10-fold lower percentage (2%) of the total and supernatant fractions loaded on the gel (results not shown). A low level of binding by the yeast SAR was discernible in the gels using 20% of the fractions, although a large portion of the total signal was observed in the supernatant fraction when equal fractions were compared (results not shown). In the more sensitive assay, it was clear that the yeast fragment bound while the TRP1 and vector fragments did not, confirming the specificity of the association between the SAR DNA and the isolated scaffold (results not shown).

Similar autoradiography gels were prepared for plasmid pB7-6 Sca/Cla, containing the RB7 tobacco SAR of SEQ ID NO:1 (results not shown). In contrast to the results obtained using the yeast SAR, above, a much larger portion of the tobacco RB7 SAR probe associated with the scaffold fraction (results not shown).

The possibility that elements other than known SARs might contribute to scaffold binding of the constructs used in expression assays was tested. Scaffold binding assays similar to those described above were conducted on restriction digests designed to separate fragments containing the CaMV 35S promoter, the GUS gene, and the nos polyadenylation signal from the control plasmid, pGHNC12. These binding assays gave uniformly negative results, even when the gel lanes were heavily overloaded with material from the pellet fraction (data not shown).

These results indicate that the RB7 SAR (SEQ ID NO:1) has a higher binding activity than that of the yeast SAR (ARS-1).

EXAMPLE 4
RB7 SAR Increases Average Expression Levels

Figure 2A:
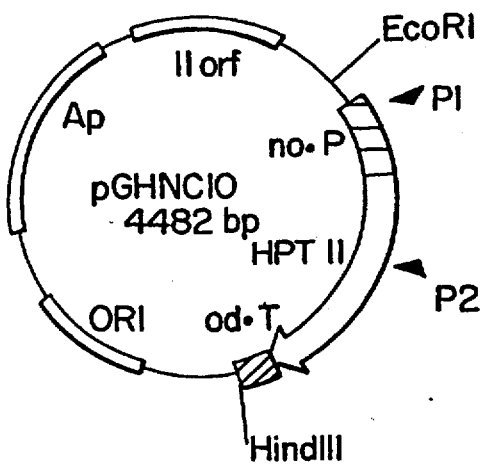
FIG. 2A is a schematic of the selection plasmid pGHNC10, where NPTII is the nptII gene from Tn5, ocs T is the polyadenylation site/terminator from octopine synthase gene, and arrows P1 and P2 indicate the locations of the PCR primers used in the estimation of copy numbers.
Figure 2B:
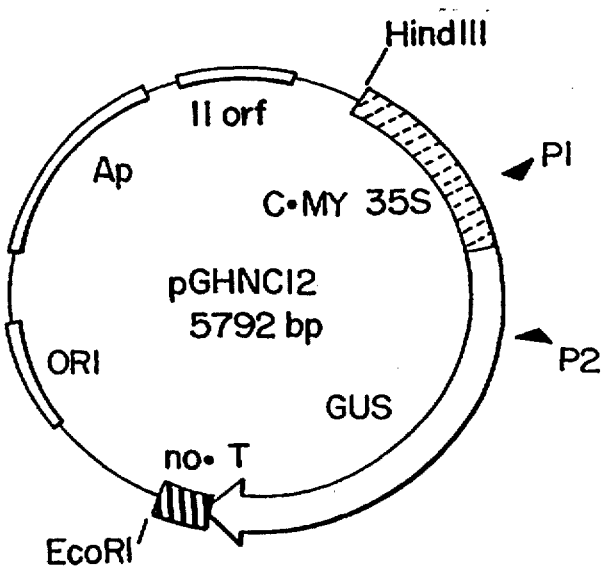
FIG. 2B is a schematic of the control expression plasmid pGHNC12, where CaMV 35S is the cauliflower mosaic virus 35S promoter, GUS is the coding region of the *E. coli* β-glucuronidase gene, nos T is the polyadenylation site/terminator from the nopaline synthase (nos) gene, and arrows P1 and P2 indicate the locations of the PCR primers used in the estimation of copy numbers.
Figure 2C:
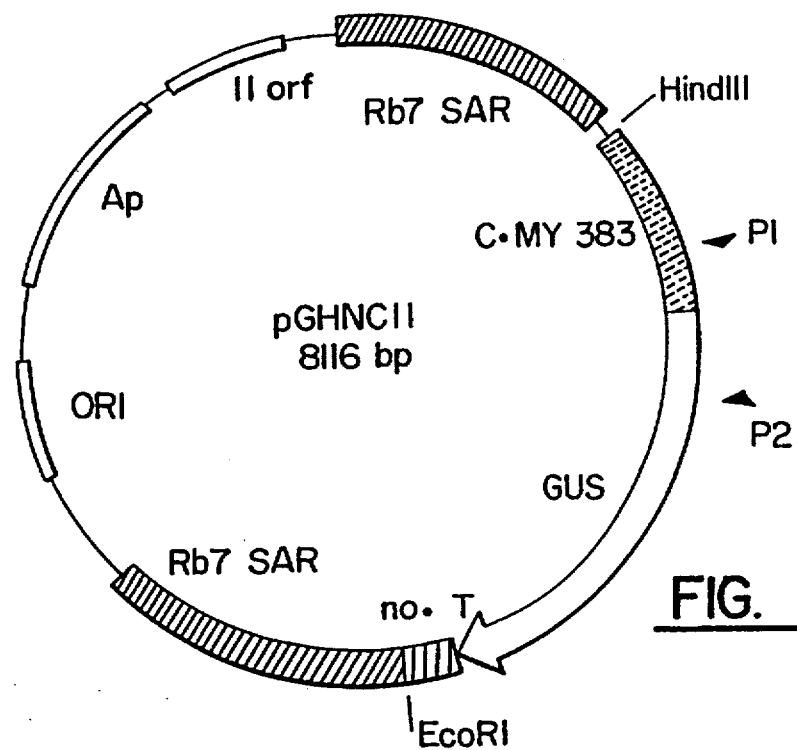
FIG. 2C is a schematic of the (+)SAR expression plasmid pGHNC11, where CaMV 35S is the cauliflower mosaic virus 35S promoter, GUS is the coding region of the *E. coli* β-glucuronidase gene, nos T is the polyadenylation site/terminator from the nopaline synthase (nos) gene, Rb7 SAR is the tobacco SAR of SEQ ID NO:1, and arrows P1 and P2 indicate the locations of the PCR primers used in the estimation of copy numbers.

Earlier studies (Allen et al., Plant Cell 5:603 (1993)) showed that flanking a GUS reporter gene with two copies of a yeast SAR element (ARS-1) increased average GUS expression by 12-fold in stably transformed cell lines. In the present Example, the same cell line was transformed with constructs similar to those of Allen et al., 1993, but using the RB7 SAR (SEQ ID NO:1). A co-transformation protocol was used to avoid physical linkage between the assayable and selectable markers (Allen et al., 1993). The constructs used are shown in FIGS. 2A, 2B and 2C.

Transformation was achieved by mixing the appropriate reporter test plasmid and the selection plasmid, co-precipitating them onto microprojectiles, and bombarding plates of tobacco suspension culture cells as described previously (Allen et al., 1993). Kanamycin-resistant ($Km^r$) microcalli were selected and each callus was used to start an independent suspension culture cell line, as described in Example 1. Histochemical staining of segments from the original microcalli showed that the staining intensity was much greater in cell lines transformed with SAR plasmids (data not shown). After three weeks of growth, with weekly transfers, suspension cells were harvested. DNA was extracted from each cell line for Southern analysis and quantitative PCR assays, and portions of the same cell population were used to measure extractable GUS activity and NPT protein levels, as described in Example 1. Transgene copy number estimates and expression data are summarized in TABLES 1 and 2.

TABLES 1 and 2 also show the mean level of GUS gene expression, measured as GUS enzyme activity, for the $KM^r$ lines. Control GUS activities averaged 8 nmol 4-MU ●$min^{-1}$●$mg$ $proteins^{-1}$, well within the range of 1 to 54 nmol 4-MU ●$min^{-1}$●$mg$ $protein^{-1}$ commonly obtained for tobacco tissue transformed with similar constructs in Agrobacterium vectors (Frisch et al., Plant J. 7:503 (1995); Hobbs et al., Plant Mol. Biol. 21:17 (1993); Jefferson et al.,

*EMBO J.* 6:3901 (1987)). When Rb7 SARs were included on both sides of the reporter gene, GUS activities averaged approximately 60-fold greater than for the control construct lacking SARs. This effect on expression is approximately five-fold greater than that of the yeast SAR previously reported (Allen et al., 1993).

TABLES 1 and 2 also show a comparison of average copy numbers for the GUS and nptII genes. These data were obtained with a quantitative PCR procedure (Allen et al., 1993). In each case, amplification was carried out with primers corresponding to sequences in the promoter and coding regions, as described in Example 1. Appropriate PCR products were quantitated by counting the radioactivity hybridized to the amplified bands, and gene copy numbers were estimated by comparing the resulting signals with a standard curve obtained in parallel for each experiment. In cell lines transformed with the construct flanked by SARS, the average 35S::GUS gene copy number was reduced by approximately two-fold compared to cell lines transformed with the control construct. This result is similar to that obtained in a previous study using the yeast SAR (Allen et al., 1993). The fact that SAR-containing lines have fewer copies of the GUS gene means that the average RB7 SAR effect on expression per gene copy is even greater than the 60-fold increase in overall expression. As shown in TABLES 1 and 2, lines transformed with the RB7 SAR construct average nearly 140-fold more GUS enzyme activity per gene copy than lines transformed with the same construct lacking SARS.

TABLE 1

| Plasmid | Cell Line | GUS Gene Copy No.[a] | GUS Activity[b] | NptII Gene Copy No.[a] | NptII protein[c] |
|---|---|---|---|---|---|
| Control (-) SARS | 12-11 | 1 | 0.9 | 2 | nd[d] |
| | 12-9 | 1 | 2.5 | 2 | 42.9 |
| | 12-46 | 1 | 0.9 | 2 | 18.4 |
| | 12-48 | 2 | 1.4 | 2 | nd |
| | 12-2 | 2 | 17.0 | 3 | 82.8 |
| | 12-13 | 4 | 0.8 | 3 | 34.6 |
| | 12-23 | 4 | 0.3 | 3 | 37.5 |
| | 12-1 | 5 | 0.5 | 3 | nd |
| | 12-40 | 6 | 1.6 | 4 | 108.5 |
| | 12-36 | 11 | 1.2 | 3 | 63.6 |
| | 12-25 | 12 | 48.4 | 8 | 50.0 |
| | 12-10 | 29 | 0.7 | 4 | 80.4 |
| | 12-37 | 33 | 7.8 | 3 | 70.2 |
| | 12-18 | 63 | 0.2 | 34 | 86.5 |
| | 12-34 | 73 | 13.0 | 14 | 76.4 |
| | 12-41 | 77 | 33.5 | 10 | 46.1 |
| Mean | | 20.2 | 8.2 | 6.2 | 61.4 |
| (+/- SE) | | +/-6.8 | +/-3.5 | +/-2.1 | +/-7.1 |
| Standard Deviation | | 27 | 14 | 8.1 | 25.5 |
| Coeff. of Variation | | 1.3 | 1.7 | 1.3 | 0.4 |

Gene copy numbers for GUS and Npt II and expression levels for the individual transgenic tobacco lines derived from co-transformations of selection plasmid with control plasmid (-SAR).
[a] = Samples were analyzed for GUS and NptII gene copy number PCR assay (Example 1).
[b] = Samples were analyzed for GUS specific activity by fluorometric assay (Example 1).
[c] = The same samples used for GUS and gene copy numbers were analyzed for NptII protein by ELISA (Example 1).
[d] = not determined
Coefficient of Variation = standard deviation/mean.

TABLE 2

| Plasmid | Cell Line | GUS Gene Copy No.[a] | GUS Activity[b] | NptII Gene Copy No.[a] | NptII protein[c] |
|---|---|---|---|---|---|
| (+) SARA | 11-36 | 1 | 0.8 | 2 | 2 |
| | 11-13 | 1 | 15.8 | 2 | 35.2 |
| | 11-8 | 1 | 818.0 | 2 | 121.3 |
| | 11-12 | 2 | 3.8 | 3 | 12.1 |
| | 11-19 | 3 | 732.0 | 3 | 17.3 |
| | 11-43 | 3 | 3109.0 | 4 | 53.9 |
| | 11-1 | 5 | 341.0 | 3 | 40.2 |
| | 11-2 | 7 | 110.0 | 4 | 19.5 |
| | 11-51 | 7 | 1241.0 | 8 | 124 |
| | 11-37 | 8 | 1006.0 | 5 | 90.9 |
| | 11-7 | 9 | 189.0 | 3 | 46.6 |
| | 11-41 | 10 | 113.0 | 3 | 24.8 |
| | 11-38 | 14 | 348.0 | 5 | 65.5 |
| | 11-18 | 15 | 378.0 | 28 | 117 |
| | 11-39 | 16 | 7.6 | 12 | 272.9 |
| | 11-23 | 20 | 4.6 | 3 | 49.5 |
| | 11-44 | 31 | 67.0 | 25 | 33.4 |
| Mean | | 9 | 499 +/- | 6.8 | 66.2 |
| (+/- SE) | | +/-2.0 | 188.2 | +/-1.9 | +/-15.9 |
| Standard Deviation | | 8.1 | 776 | 7.8 | 65.7 |
| Coeff. of Variation | | 0.9 | 1.6 | 1.1 | 1.0 |

Gene copy numbers for GUS and Npt II and expression levels for the individual transgenic tobacco lines derived from co-transformations of selection plasmid with control plasmid (-SAR).
[a] = Samples were analyzed for GUS and NptII gene copy number PCR assay (Example 1).
[b] = Samples were analyzed for GUS specific activity by fluorometric assay (Example 1).
[c] = The same samples used for GUS and gene copy numbers were analyzed for NptII protein by ELISA (Example 1).
[d] = not determined
Coefficient of Variation = standard deviation/mean.

EXAMPLE 5

Transient Expression

To distinguish effects that depend on chromosomal integration from general transcriptional enhancer activity, SAR constructs were tested in a transient expression system. Such assays are widely used in studies of transcriptional enhancers. Transiently transfected DNA is poorly organized into nucleosomes (Archer et al., *Science* 255:1573 (1992); Weintraub *Cell* 42:705 (1985)) and the fact that only a small minority of expressing cells go on to become stably transformed suggests that most transient expression occurs without chromosomal integration (Christou, *Plant J.* 2:275 (1992); Davey et al., *Plant Mol. Biol.* 13:273 (1989); Paszkowski et al., *EMBO J.* 3:2717 (1984); Saul and Potrykus, *Develop. Genet.* 11:176 (1990)). When the plant SAR plasmid (pGHNC11) was electroporated into NT-1 protoplasts prior to GUS assay 20 hours later, an approximately three-fold increase in GUS gene expression was observed, from 2.7 to 7.2 nmol-min-$^{-1}$-mg proteins$^{-1}$, as compared to those transfected with the control plasmid lacking SARs. These results are in sharp contrast to the nearly 60-fold increase in overall expression, or the nearly 140-fold increase in expression per gene copy in stably transformed cell lines as reported in Example 5. The effect of the RB7 element in stably transformed lines thus was 20–50 times greater than its effect in transient transcription assays. These results indicate that the RB7 element is not simply acting as a transcriptional enhancer.

EXAMPLE 6

Integration Patterns

Direct gene transfer procedures can result in complex integration patterns (Christou *Plant J.* 2:275 (1992); Koziel et al., *Bio/Technology* 11:194 (1993); Mittlesten Scheid et al. *Mol. Gen. Genet.* 228:104 (1991); Paszkowski et al., *EMBO J.* 3:2717 (1984); Tomes et al. *Plant Mol. biol.* 14:261 (1990); Wan and Lemaux, *Plant Physiol.* 104:37 (1994)). Therefore, multiple cell lines transformed with either the control expression plasmid (pGHNC12) or the RB7 SAR(+) expression plasmid (pGHNC11) were compared by DNA gel blot analysis (according to Example 1) following digestion of isolated genomic DNA with EcoRI and HindIII, which cut on either side of the 35S::GUS::nos cassette (see FIG. 2).

Genomic DNA (10 μg) was digested with HindIII/EcoRI was fractionated on a 0.85% agarose gel. The DNA was blotted to nylon membranes and probed as described in Example 1. Gel lanes contained 10 μg HindIII/EcoRI digested genomic DNA from the respective cell lines transformed with the SAR(+) or (-)SAR control plasmids. Also probed were copy number reconstruction gel lanes, containing 10 μg of non-transformed (control) genomic DNA spiked with the equivalent of 40, 20, 10, 5, 1 and 0 copies of the 2.8 kb 35S::GUS::nos T per 1 C equivalent.

When probed with sequences from the 35S promoter, digests of the parent plasmids yielded a single band of 2.8 kb (data not shown). After integration into genomic DNA, complex hybridization patterns were observed, indicating extensive rearrangement during the integration process. Integration patterns for the control construct were somewhat more complex, on average, than those for the SAR plasmid. However, this difference may reflect the lower average copy number in the SAR lines (see above). There was no obvious difference in the complexity of integration patterns for SAR and control lines with similar copy numbers.

Intact 2.8 Kb fragments containing the 35S::GUS gene were observed in most transformants, suggesting that most cell lines contained some non-rearranged gene copies. However, approximately 20–30% of the recovered lines lacked the 2.8 Kb band indicative of intact 35S::GUS genes. Generally this band was missing from lines with low overall copy numbers and with few, if any, bands with an intensity equal to or greater than the single copy reconstruction standard. Expression levels were generally very low; most of these lines likely contained genes with rearrangements in the promoter region that reduced or eliminated their activity. One exception was the SAR line 37 (11–37), for which PCR analysis gave an estimate of eight copies and Southern analysis showed several high molecular weight bands of multicopy intensity. This cell line also had high GUS expression (TABLE 2), indicating that in this instance the rearrangement did not dramatically affect gene function.

Gel blots of unrestricted DNA samples were also probed (data not shown). Samples were selected to represent a variety of copy numbers and expression levels. Undigested DNA (5 μg) from cell lines, selected to include a wide range of gene copy numbers and expression levels, was fractionated on a 0.6% agarose gel and analyzed with a 501 bp CaMV35S probe. The position of high molecular weight chromosomal DNA was determined by ethidium bromide staining. The positions of undigested plasmid (pGHNC11 and pGNHC12) were determined. Also probed were lanes representing 30, 10, 3 and 1 copies of the CaMV 35S::GUS-::nos T per 1 C, spiked in 5 μg of non-transformed genomic DNA.

In each case, all detectable GUS sequences migrated with high molecular weight chromosomal DNA, ruling out the possibility that they were maintained on extrachromosomal elements similar in size to the plasmids used in transformation. Similar results were obtained for lines with low and high overall copy numbers.

Chen et al., *Plant J.* 5:429 (1994) reported that transgenes in wheat cell lines subjected to direct DNA transfer may sometimes contain N-6-methyladenine, raising the possibility that transformation of an endophyte, such as a mycoplasma-like organism, occurred simultaneously with transformation of the wheat cells. To exclude this possibility, a methylation analysis was carried out.

Figure 3A:
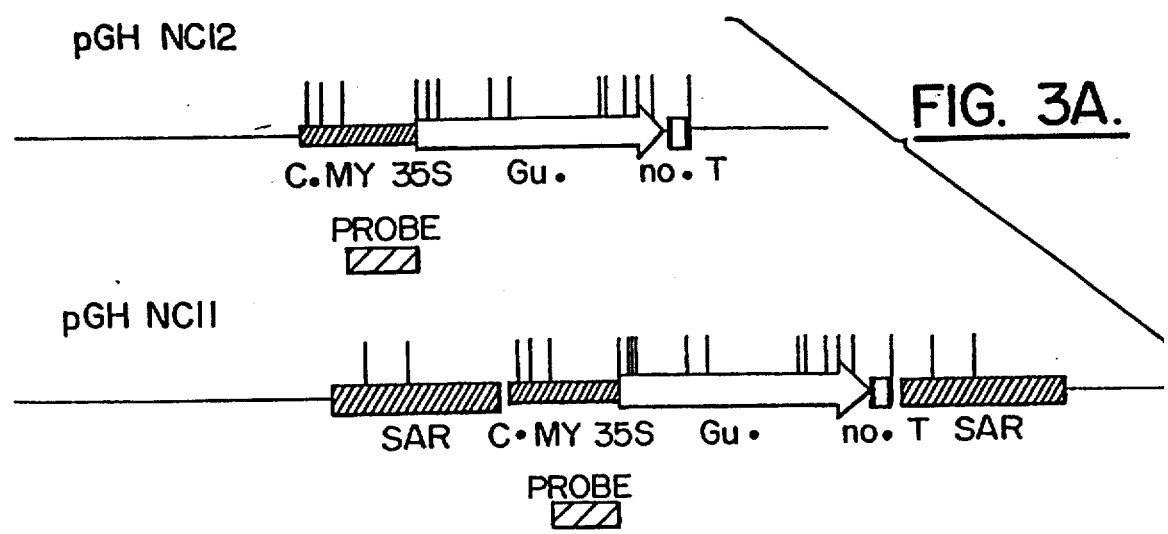
FIG. 3A is a restriction map showing the GATC sites (vertical lines) for RB7 SAR(+) plasmid pGHNC11 and the SAR(−) control plasmid pGHNC12. A 501 base pair probe fragment from the CaMV 35S promoter is indicated below the restriction maps.
Figure 3B:
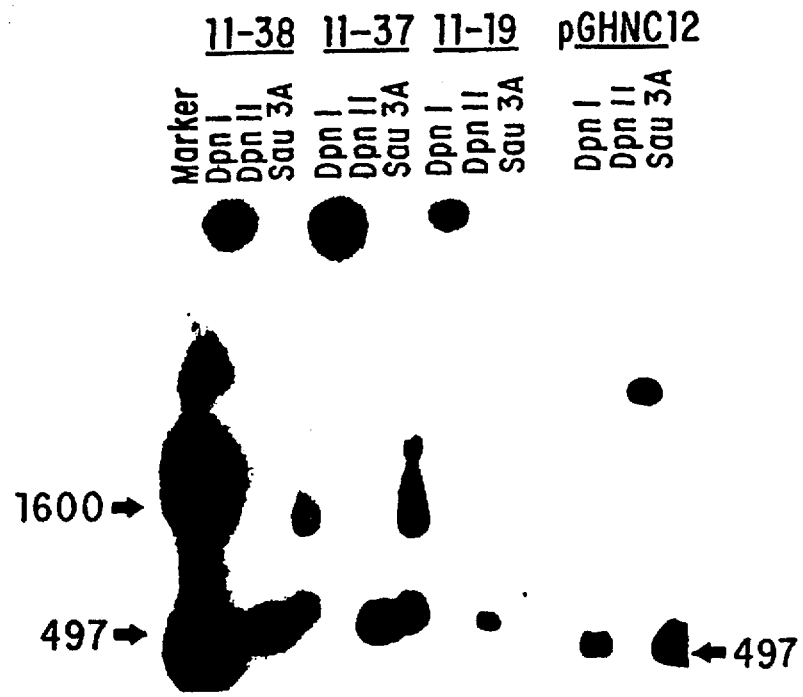
FIG. 3B provides DNA gel blots of selected RB7 SAR(+) lines (left panel) and a control of plasmid pGHNC12 (right panel), indicating DpnI, DpnII and Sau3A digests. Arrows indicate molecular weights estimated from 1 kb markers.
Figure 3C:
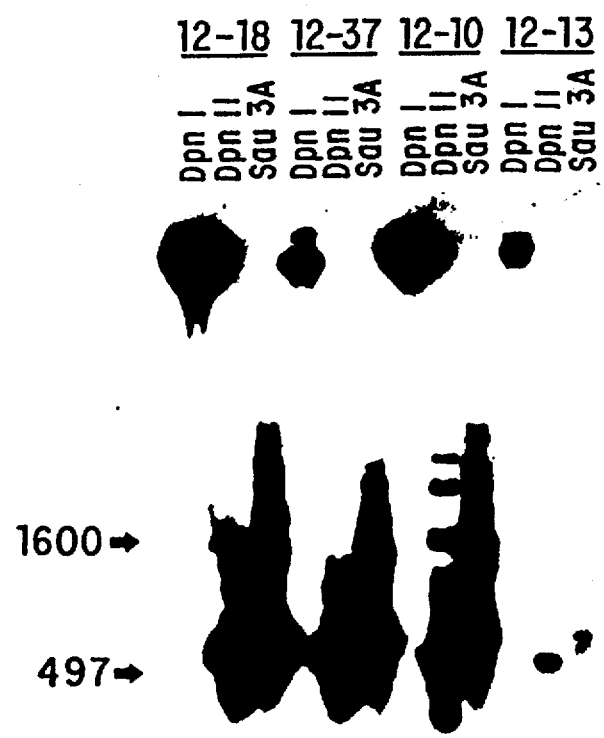
FIG. 3C is a DNA gel blot of selected SAR(−) control lines showing DpnI, DpnII and Sau3A digests. Molecular weight estimates are indicated by arrows.

High molecular weight DNA from cell lines selected to include a variety of GUS gene copy numbers and expression levels was prepared and digested with the isoschizomers DpnI, DpnII, or Sau3A. DpnI requires N-6-adenine methylation; DpnII is inhibited by adenine methylation; Sau3A is unaffected by N-6-adenine methylation but inhibited by cytosine methylation. FIG. 3A is a restriction map showing the GATC sites (vertical lines) for SAR(+) plasmid pGHNC11 and the SAR(-) control plasmid pGHNC12. The 501 base pair probe fragment from the CaMV 35S promoter is indicated below the restriction maps. FIG. 3B is a DNA gel blot of selected SAR(+) lines showing DpnI, DpnII and Sau3A digests. Molecular weights are estimated (arrows) from 1 kb markers (BRL). The control digest of plasmid pGHNC12 which was produced from a Dam methylase (+) *E. coli* strain is shown in the right panel. FIG. 3C is a DNA gel blot of selected SAR(-) control lines showing DpnI, DpnII and Sau3A digests. Molecular weight estimates are shown by arrows to the left of the panel.

DpnI, which requires N-6-adenine methylation for activity, does not cut transgene DNA but does completely digest the same sequence in *E. coli* plasmid DNA used for transformation. DpnII, an isoschizomer that differs from DpnI in that it is inhibited by adenine methylation, does not cut the plasmid DNA, but extensively cleaves transgene sequences in all tested cell lines. Another GATC-cleaving isoschizomer, Sau3A completely digests plasmid DNA, but shows only partial activity on transgene DNA. This enzyme is inhibited by cytosine methylation at the C residue in the GATC target sequence. In plant DNA, cytosine methylation occurs preferentially to CG and CXG sites in plant DNA (Gruenbaum et al., Nature 292:860 (1981)), although some methylation of cytosines also occurs in non-symmetrical positions (Meyer et al., *Embo J.* 13:2084 (1994)). Failure of Sau3A to fully cleave transgene DNA is thus consistent with the presence of cytosine methylation at some of the GATC sites in the transgene. Taken together, these data indicate that adenine methylation has been lost and a plant-specific pattern of cytosine methylation has been established during replication of the transgene in the transformed cell lines.

EXAMPLE 7
Copy Numbers and Expression Levels

GUS specific activity as nmols 4-MU produced ●min$^{-1}$●mg protein$^{-1}$ was determined by fluorimetry, and gene copy number was determined by the PCR procedure, for multiple transgenic cell lines eight weeks after transformation, as described in Example 1.

Figure 4:
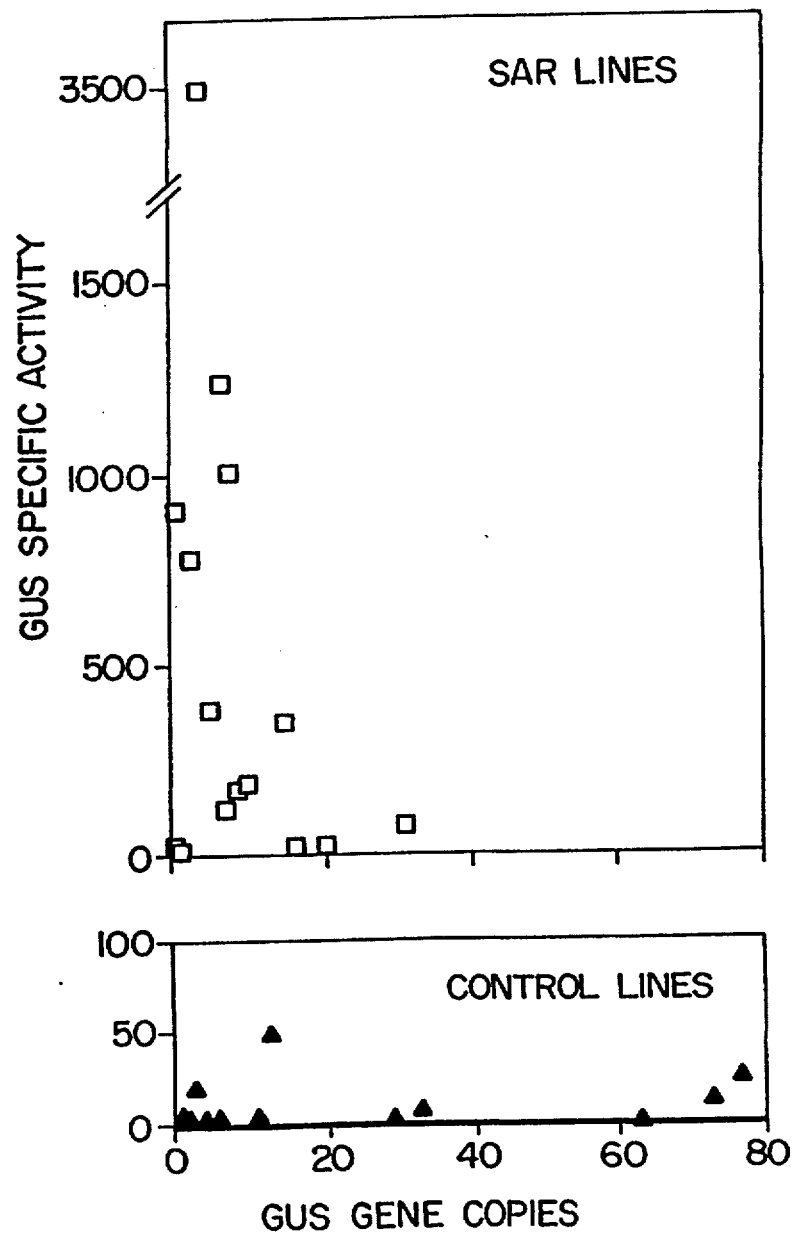
FIG. 4 plots GUS expression versus gene copy number for individual cell lines, where open squares represent RB7 SAR(+) transformants and closed triangles represent controls.
Figure 5:
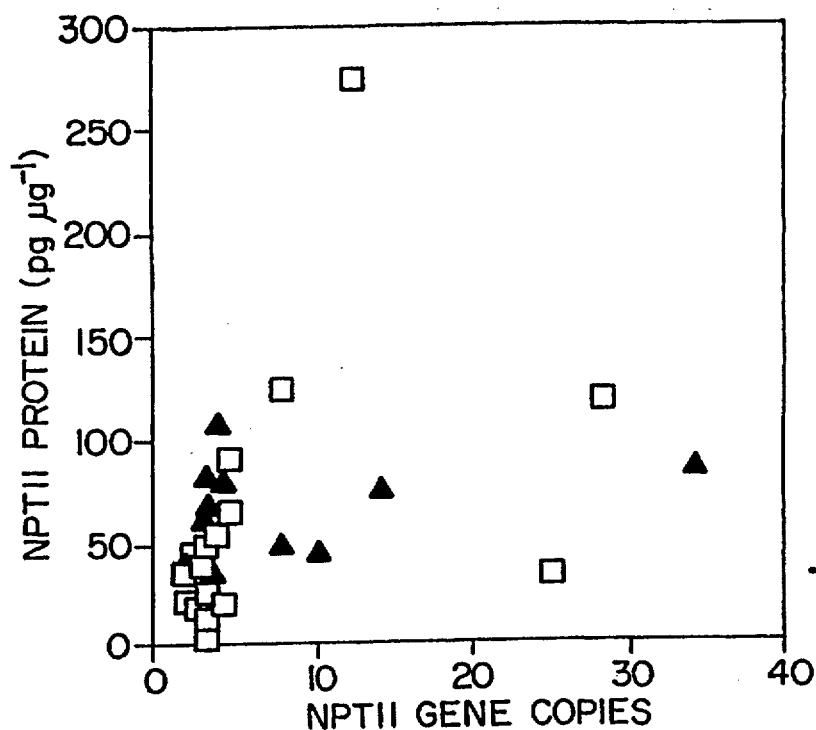
Figure 6:
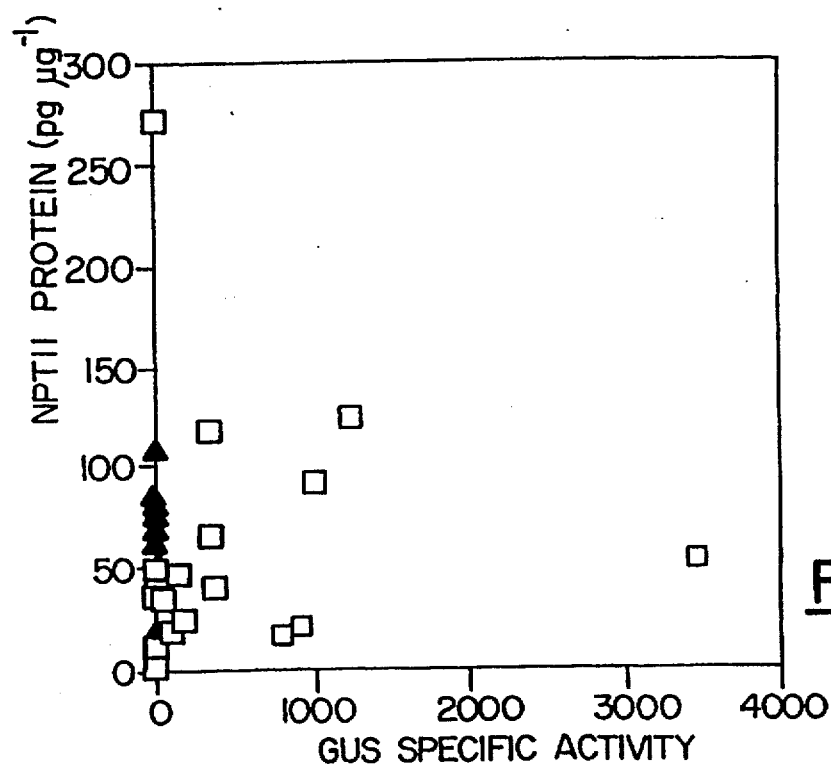

FIG. 4 plots GUS expression versus gene copy number for individual cell lines (open squares=RB7 SAR(+) transformants; closed triangles=control lines). The largest RB7 SAR effects were obtained in cell lines with smaller numbers of transgenes (about 20 or fewer copies per cell), and expression of both SAR and control constructs was low in lines with high copy numbers. Although the overall degree of stimulation was much greater for the plant SAR, the relationship to transgene copy number was quite similar to that previously observed in experiments with a weaker SAR from the yeast ARS-1 element (Allen et al., *Plant Cell* 5:603 (1993)). Increased expression of the yeast SAR construct was seen in transformants carrying as many as 30–40 copies of the transgene. In the present Example, the effects of the RB7 SAR were most evident in lines carrying fewer than about 20 copies.

Three cell lines (11-12, 11-13, and 11-36) containing the SAR construct at low copy number also showed low GUS expression, apparent exceptions to the general rule that low copy numbers are associated with high expression (TABLE 2). These lines were among those lacking the intact 2.8 Kb 35S::GUS::nos T band (see Example 7), and thus may contain only rearranged transgene sequences. These data have only a small effect on the overall data analysis, however. Eliminating data from the SAR and control lines lacking the 2.8 Kb band provides an average GUS activity of 574 nmols 4-MU ●min$^{-1}$mg protein$^{-1}$ for lines containing the SAR construct as compared to 10.4 nmols 4-MU ●min$^{-1}$●mg proteins$^{-1}$ for control lines, a 55-fold difference. Corresponding values for the entire data set were 499 and 8.2 nmols 4-MU●min$^{-1}$●mg protein$^{-1}$, a 61-fold difference.

EXAMPLE 8
Effects of Co-Transformation on Expression of Selection Gene

In the present data, the Rb7 SAR of SEQ ID NO:1 increased expression to a greater degree when low numbers of the transgene were present and, when higher numbers of the transgene are present, expression of both SAR and control constructs fell to low values. These data indicate that the present SARs were not acting as transcriptional insulators, and/or that variation from sources other than chromosomal position effects dominates transgene expression.

Figure 6:
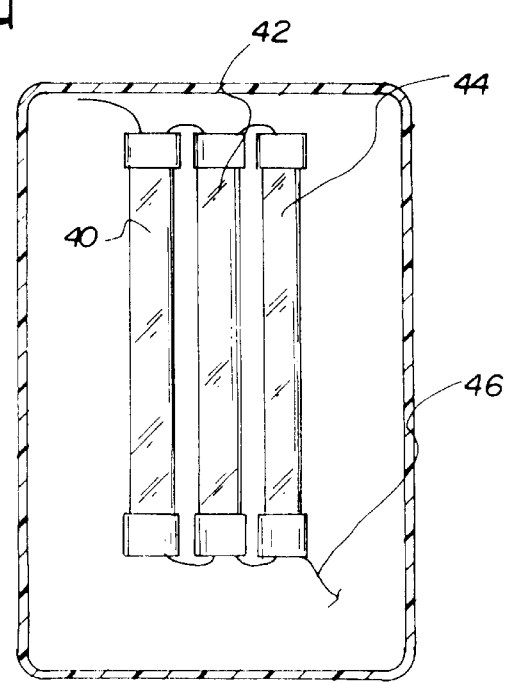
FIG. 6 incorporates data from FIGS. 4 and 5, re-plotted to compare the expression levels for each introduced gene. Open squares represent double RB7 SAR transformants; closed triangles represent control lines.

To determine whether co-transformation with a SAR-containing reporter plasmid resulted in increased expression of the nptII gene on the selection plasmid, the NPT protein levels in extracts of the same cell suspensions were measured using an ELISA assay. As shown in TABLE 2, co-transformation with the SAR-containing vector had no effect (1.1-fold) on average NPT protein abundance for all cell lines. NPTII protein (pg/μg total protein) was determined by ELISA, and gene copy number was determined by the PCR procedure for the transgenic cell lines used for GUS analysis (see FIG. 4). FIG. 5 is a plot of NPT protein against gene copy number (SAR(+) transformants=open squares; control lines=closed triangles), showing that NPTII expression was unaffected by co-transformation with the SAR constructs. NPTII protein levels vary widely in different transformants, up to about 100 pg/ug cellular protein. The GUS and NPTII expression data from FIGS. 4 and 5 were re-plotted to compare the expression levels for each introduced gene (FIG. 6). Open squares represent double SAR transformants; closed triangles represent control lines. Plotting GUS activity against NPT protein level showed that there is only a weak correlation between NPTII and GUS expression. Nearly all the NPT values for SAR lines fall within the range of variation seen for control lines.

These results indicate that even though co-transformation often results in integration at the same genetic locus (Christou and Swain, *Theor. Appl. Genet.* 79:337 (1990); Christou et al., *Proc. Natl. Acad. Sci. USA* 86:7500 (1989); McCabe et al., *Bio/Technology* 6:923 (1988); Christou, *Plant J.* 2:275 (1992); Saul and Potrykus, *Develop. Genet.* 11:176 (1990)), genes on co-transformed plasmids can be substantially independent in their expression. If the reporter and selection plasmids were integrated in a closely interspersed array, SARs on the GUS reporter construct might have also stimulated nptII gene expression. The lack of any such effect implies that the two plasmids normally do not integrate in a closely interspersed pattern, or that intervening plasmid sequences prevent the SARs from affecting other genes at the same chromosomal site.

The foregoing examples are illustrative of the present invention, and are not to be construed as limiting thereof. The invention is described by the following claims, with equivalents of the claims to be included therein.

---

That which is claimed is:

1. An isolated DNA molecule having a nucleotide sequence of SEQ ID NO:1.

2. A DNA construct comprising, in the 5' to 3' direction, a transcription initiation region, a structural gene positioned downstream from said transcription initiation region and operatively associated therewith, and a scaffold attachment region having SEQ ID NO:1 positioned either 5' to said transcription initiation region or 3' to said structural gene.

3. A DNA construct according to claim 2, which construct comprises, in the 5' to 3' direction, a first scaffold attachment region having SEQ ID NO:1, a transcription initiation region, a structural gene positioned downstream from said transcription initiation region and operatively associated therewith, and a second scaffold attachment region having SEQ ID NO:1.

4. A DNA construct according to claim 2 carried by a plant transformation vector.

5. A plant cell containing a DNA construct according to claim 2.

6. A dicotyledonous plant cell containing a DNA construct according to claim 2.

7. A monocotyledonous plant cell containing a DNA construct according to claim 2.

8. A gymnosperm plant cell containing a DNA construct according to claim 2.

9. A recombinant plant comprising transformed plant cells, said transformed plant cells containing a heterologous DNA construct comprising, in the 5' to 3' direction, a transcription initiation region functional in plant cells, a structural gene positioned downstream from said transcription initiation region and operatively associated therewith, and a scaffold attachment region having SEQ ID NO:1 positioned either 5' to said transcription initiation region or 3' to said structural gene.

10. A recombinant plant according to claim 9, which construct comprises, in the 5' to 3' direction, a first scaffold attachment region having SEQ ID NO:1, a transcription initiation region, a structural gene positioned downstream from said transcription initiation region and operatively associated therewith, and a second scaffold attachment region having SEQ ID NO:1.

11. A recombinant plant according to claim 10, wherein said construct further comprises a termination sequence positioned downstream from said structural gene and operatively associated therewith, said termination sequence positioned 5' to said second scaffold attachment region.

12. A recombinant plant according to claim 9, which plant is a monocot.

13. A recombinant plant according to claim 9, which plant is a dicot.

14. A recombinant plant according to claim 9, which plant is a dicot selected from the group consisting of tobacco, potato, soybean, peanuts, cotton, and vegetable crops.

15. A recombinant plant according to claim 9, which plant is a gymnosperm.

16. A method of making transgenic plant cells having increased expression of foreign genes therein, said method comprising:

providing a plant cell capable of regeneration;

transforming said plant cell with a DNA construct comprising, in the 5' to 3' direction, a transcription initiation region, a structural gene positioned downstream from said transcription initiation region and operatively associated therewith, and a scaffold attachment region having SEQ ID NO:1 positioned either 5' to said transcription initiation region or 3' to said structural gene.

17. A method according to claim 16, which construct comprises, in the 5' to 3' direction, a first scaffold attachment region having SEQ ID NO:1, a transcription initiation region, a structural gene positioned downstream from said transcription initiation region and operatively associated therewith, and a second scaffold attachment region having SEQ ID NO:1.

18. A method according to claim 16, wherein said transforming step is carried out by bombarding said plant cell with microparticles carrying said expression cassette.

19. A method according to claim 16, wherein said plant cell resides in a plant tissue capable of regeneration.

20. A method according to claim 16, further comprising the step of regenerating shoots from said transformed plant cells.

21. A method according to claim 16, further comprising the step of regenerating roots from said transformed plant cells.

22. A method according to claim 16, further comprising the step of regenerating a plant from said transformed plant cells.

23. A method according to claim 16, wherein said plant cells are monocot cells.

24. A method according to claim 16, wherein said plant cells are dicot cells.

25. A method according to claim 16, wherein said plant cells are gymnosperm plant cells.

26. A method of making recombinant tobacco plant cells having increased expression of foreign genes therein, said method comprising:

providing a tobacco plant cell capable of regeneration;

transforming said tobacco plant cell with a DNA construct comprising, in the 5' to 3' direction, a transcription initiation region functional in plant cells, a structural gene positioned downstream from said transcription initiation region and operatively associated therewith, and a scaffold attachment region having SEQ ID NO:1 positioned either 5' to said transcription initiation region or 3' to said structural gene.

27. A DNA construct comprising, in the 5' to 3' direction, a transcription initiation region, a structural gene positioned downstream from said transcription initiation region and operatively associated therewith, and a scaffold attachment region having SEQ ID NO:1 positioned either 5'0 to said transcription initiation region or 3' to said structural gene;

which DNA construct is carried by a plant transformation vector.

28. A recombinant tobacco plant comprising transformed tobacco plant cells, said transformed tobacco plant cells containing a heterologous DNA construct comprising, in the 5' to 3' direction, a transcription initiation region functional in plant cells, a structural gene positioned downstream from said transcription initiation region and operatively associated therewith, and a scaffold attachment region having SEQ ID NO:1 positioned either 5' to said transcription initiation region or 3' to said structural gene.

* * * * *

UNITED STATES PATENT AND TRADEMARK OFFICE
CERTIFICATE OF CORRECTION

PATENT NO. : 5,773,695

DATED : June 30, 1998

INVENTOR(S) : William F. Thompson, Gerald Hall Jr., Steven Spiker, George C. Allen It is certified that error appears in the above-identified patent and that said Letters Patent is hereby corrected as shown below:

In the drawings, Sheet 1 (Figures 1, 2A, 2B); Sheet 2 (Figs. 2C, 3A); Sheet 3 (Figs. 3B, 3C); Sheet 4 (Fig.4); Sheet 5 (Figs. 5, 6) should appear as per the attached sheet of drawings.

On the cover sheet, column 2, please replace "28 Claims, 3 Drawing Sheets" with -- 28 Claims, 5 Drawing Sheets --.

In claim 27, at column 22, line 64, please replace "5'0" with -- 5' --.

Signed and Sealed this

First Day of December, 1998

Attest:

BRUCE LEHMAN

*Attesting Officer*    *Commissioner of Patents and Trademarks*